United States Patent
Drake et al.

(10) Patent No.: US 7,989,213 B2
(45) Date of Patent: Aug. 2, 2011

(54) SURFACE ENHANCED RESONANCE RAMAN SCATTERING SPECTROSCOPY (SERRS) NANOPARTICLE PROBES AND METHODS OF USE

(75) Inventors: Philip Leslie Drake, Taipei (TW); Hsiang-Yuan Huang, Kaohsiung (TW)

(73) Assignee: Industrial Technology Research Institute, Hsinchu (TW)

( * ) Notice: Subject to any disclaimer, the term of this patent is extended or adjusted under 35 U.S.C. 154(b) by 218 days.

(21) Appl. No.: 12/485,443

(22) Filed: Jun. 16, 2009

(65) Prior Publication Data

US 2010/0255599 A1 Oct. 7, 2010

Related U.S. Application Data

(60) Provisional application No. 61/061,711, filed on Jun. 16, 2008.

(51) Int. Cl.
*G01N 21/75* (2006.01)
*G01N 31/22* (2006.01)
(52) U.S. Cl. ........ 436/164; 436/169; 436/171; 436/172; 422/400; 422/420
(58) Field of Classification Search .................. 422/400, 422/420
See application file for complete search history.

(56) References Cited

U.S. PATENT DOCUMENTS 7,897,408 B2 * 3/2011 Iwahori ......................... 436/172

OTHER PUBLICATIONS

Drake et al. "Design of a Peptide Linker Group to Increase the Surface Enhanced Raman Spectroscopy Signal Intensity of a Rhodamine_Nanoparticle System", Journal of Analytical Chemistry, 2010, vol. 65, No. 6, pp. 608-613.*

* cited by examiner

*Primary Examiner* — Yelena G Gakh
(74) *Attorney, Agent, or Firm* — Birch, Stewart, Kolasch & Birch, LLP

(57) ABSTRACT

Disclosed are Surface Enhanced Resonance Raman Spectroscopy (SERRS) probes and their use in detection methods for bioassays. Further disclosed is signal optimization of surface enhanced resonance Raman probes achieved by chemical modification of the probes. Also disclosed are methods for increasing the Raman cross-section by varying the chemical composition of a linker group linking a signal molecule to a nanoparticle surface. The signal molecules, such as dyes, may be modified with a linker group designed to both enhance the SERRS signal and to couple the signal molecule to the nanoparticle surface.

13 Claims, 11 Drawing Sheets

(1e)

(2e)

(3e)

SURFACE ENHANCED RESONANCE RAMAN SCATTERING SPECTROSCOPY (SERRS) NANOPARTICLE PROBES AND METHODS OF USE

This application claims priority to U.S. Provisional Application No. 61/061,711, filed Jun. 16, 2009, the entire contents of which are herein incorporated by reference.

TECHNICAL FIELD

The present disclosure is directed to surface enhanced resonance Raman probes and their use in detection methods for bioassays. The present disclosure is further directed to signal optimization of surface enhanced resonance Raman probes achieved by chemical modification of the probes.

BACKGROUND

Surface Enhanced Raman Spectroscopy (SERS) and Surface Enhanced Resonance Raman Spectroscopy (SERRS) have been used as analytical tools for many years (1, 2). SERS active particles have been successfully employed as labels or probes in chemical assays (3), immunoassays (4, 5, 6), and DNA detection (7, 8), with the SERS peak intensity being correlated to the concentration of target species.

SERS was first discovered in 1974 by Fleischmann et al. (9) when they recorded intense Raman signals from pyridine adsorbed on roughened silver electrodes in aqueous solutions. Later, several publications concluded that these intense signals could not be accounted for by conventional Raman theory and suggested an enhancement mechanism was taking place at the metal surface, increasing the scattering intensity from each adsorbed pyridine molecule (10, 11). Since then, other publications have documented this surface enhancement effect and several theories have been proposed to account for it. Review articles describe this historical and theoretical development in detail (12, 13, 14).

Surface Enhanced Resonance Raman Spectroscopy (SERRS) combines SERS with the resonance enhancement effect associated with dye molecules (15, 16). In SERRS experiments, the dye adsorption overlaps with the Surface Plasmon Resonance (SPR) of the metal nanoparticle (NP) and the excitation laser used. The combined effect of the resonance and surface enhancement makes SERRS one of the most sensitive forms of spectroscopy available.

Both SERS and SERRS have been used for single molecule detection (17, 18). The large enhancement factors observed in SERRS experiments have been attributed to two factors, chemical enhancement and electromagnetic enhancement. Chemical enhancement is believed to result from charge transfer from the molecule to the metal surface or visa versa (19). Electromagnetic enhancement is believed to result from the localized SPR associated with the metal NP. This SPR effect greatly enhances the electromagnetic field at the surface of the NP (20). Other factors may effectively increase the Raman cross-section, such as resonance effects from a chromophore, or the presence of specific cations or anions (21).

Other publications have shown the SERS enhancement effect to be extremely large, of the order of $10^{12}$ fold, and that the use of SERRS may lead to single molecule sensitivity (22).

Unlike a fluorescent probe, a Raman probe has several structural components, such as a central nanoparticle core, a linker group, and a chromophore. Variations in the nanoparticle composition and size, the linker composition and length, and the chromophore type and number density, all potentially effect the Raman signal from the probe.

The metallic nanostructure gives rise to surface plasmon resonances. The chromophore provides chemical enhancement of the Raman signal. The energy flow and resonance coupling between the nanoparticle and the chromophore give rise to the SERRS effect. If the chromophore is too far away from the nanostructure, no coupling will occur and the Raman signal will be reduced. Chemical bonding between the chromophore and the nanoparticle also plays an important role (23).

The demonstration of the ability of SERRS to deliver single molecule sensitivity has led to much research in this area. For instance, the following US patent publications and patents provide examples of the application of this technology: U.S. Patent Application Publication No. 2007/0155021, U.S. Patent Application Publication No. 2005/0221510, U.S. Pat. No. 5,445,972, and U.S. Pat. No. 7,192,778. These SERRS applications and patents are largely directed to the use of silica surfaces coated with a metallic layer, and variations in the operation and configuration of Raman devices. Most are directed to the field of SERS active particles, as opposed to surfaces, as disclosed in U.S. Patent Application Publication No. 2007/0155021. These disclosures are based on a SERS active particle having a cationic coating. They claim that previously published methods make particles with an anionic character and that the changing of this coating to be cationic provides improvements in both signal strength and reproducibility. These prior disclosures make use of 'surface seeking groups' as a way of improving the Raman signal.

U.S. Pat. No. 5,445,972 discloses the use of Raman active labels attached to specific binding members for use in ligand-binding assays. However, this patent does not specify the use of metallic nanoparticles as a component of the Raman label and appears to cover the use of Raman active dye molecules, but not Raman active particles. Such techniques are a modification of the Raman dye with standard Ag surfaces or Ag nanoparticles used to obtain the full SERS signal. In these earlier techniques, Ag nanoparticles and Ag coated surfaces are used to produce the Raman signal from the Raman active label.

U.S. Pat. Nos. 7,192,778 and 6,861,263 disclose the use of metallic nanoparticles coated with a $SiO_2$ layer. This technique comprises trapping the Raman active molecules in the $SiO_2$ layer. The glass layer serves several functions. For instance, the glass layer keeps the Raman active molecules trapped on the surface of the nanoparticle, keeps the nanoparticle solution stable in a variety of different solvents, and acts as a point of modification when attaching other species to the whole particle structure. These patents also disclose the use of 'sandwich' structures, wherein the Raman active molecules are located at the junction between two metallic nanoparticles.

U.S. Patent Application Publication No. 2005/0130163 discloses a similar technique but specifies that the Raman active particle consists of more than one metallic nanoparticle dispersed in a polymer shell, wherein the polymer material may be any common polymer and glass structure.

U.S. Patent Application Publication No. 2006/0246460 describes a system for DNA detection using two Raman active molecules. In the initial state both Raman molecules are on the nanoparticle surface and so both contribute to the overall Raman signal. Upon binding the target DNA, one of the Raman molecules is removed from the nanoparticle surface and the overall Raman signal changes.

U.S. Pat. No. 6,219,137 discloses core-shell structures, but specify that the analyte provides the Raman signal. That is, the nanoparticle core shell structure has no Raman signal itself. The nanoparticle core shell structure only has a Raman signal when the target analyte binds to the metallic SERS surface. Only then is the Raman spectra obtained.

SUMMARY

The present disclosure relates to the use of SERRS active particles. In particular, the present disclosure provides new SERRS active particles and methods of optimizing SERRS active particles by modifying a linker group between a nanoparticle (e.g., metal nanoparticle) and a signal molecule, as well as methods of detecting an analyte by attaching the modified SERRS active particles either, directly or indirectly, via a recognition species, to the analyte. The SERRS signal from the SERRS active particle may then be correlated with the concentration of the analyte, thereby allowing quantification of the analyte.

The present disclosure provides methods designed to increase the Raman signal intensity of a nanoparticle probe in SERRS applications, thereby improving the detection limit of the probe when used as a label, for instance, in a chemical assay or a bioassay. The increase in Raman intensity is achieved by the use of a linker group used to couple signal molecules, such as dyes, to the surface of nanoparticles, such as Au or Ag nanoparticles.

The SERRS active particles of the present disclosure are particles (e.g., nanoparticles) to be coated with signal molecules, wherein the signal molecules are modified with the a linker group.

DETAILED DESCRIPTION

Figure 1:
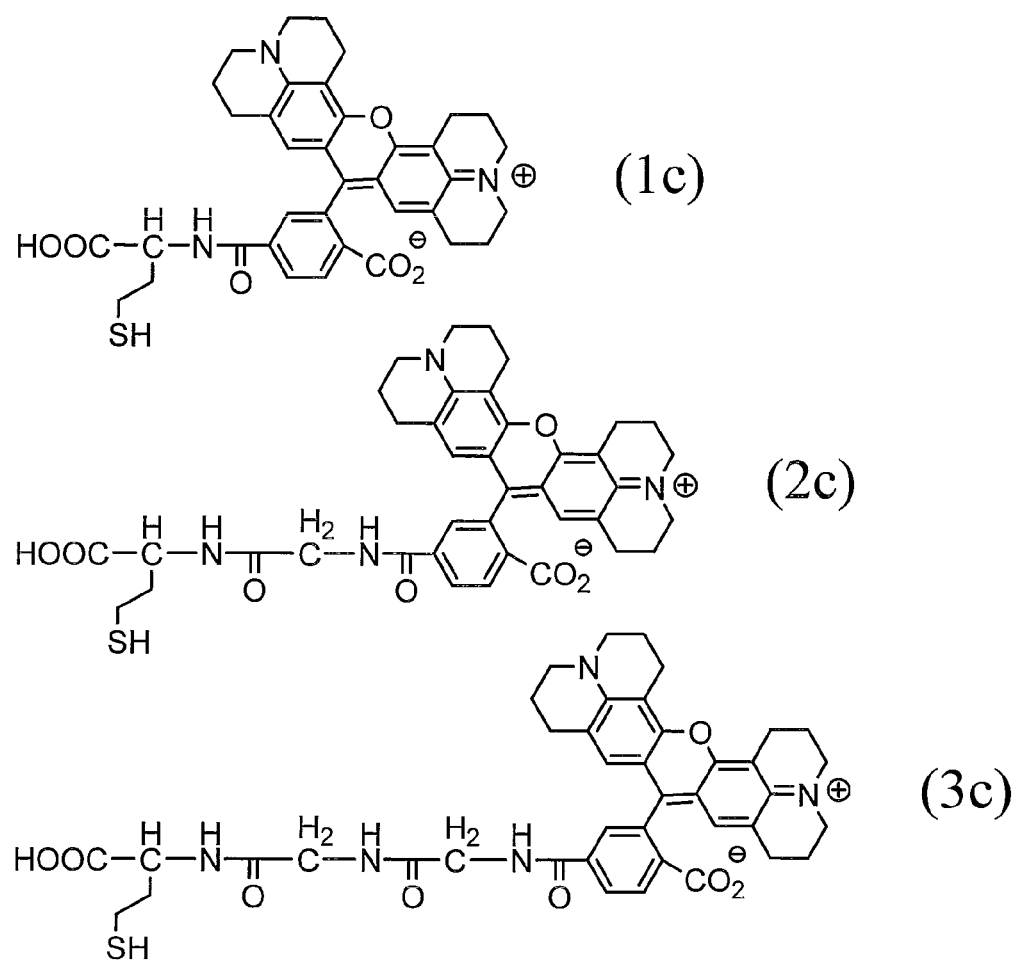
FIG. 1: Depiction of the structure of the three modified carboxy-x-rhodamine dyes.

None of the earlier reports disclose or suggest the synthesis and use of a linker group between the Raman dye and the nanoparticle, and the highly beneficial effect this has on the signal strength and reproducibility. The present disclosure explains for the first time a clear enhancement achieved by the addition of a linker between the signal molecule and the surface seeking group. The present invention utilizes a Raman label which is a complete structure, containing a central metallic nanoparticle coated with Raman active signal molecules. The present disclosure does not require a $SiO_2$ layer since the Raman active signal molecule is attached to the nanoparticle through a chemical bond. In the present disclosure, the metallic nanoparticle has a Raman signal molecule permanently attached to the surface, providing the nanoparticle with an inherent Raman signal. Even in the absence of the target, the presently disclosed probe particles still possess a Raman signal. This means that the presently disclosed probes can be used to detect analytes that are not intrinsically Raman active.

The present disclosure provides for probes which display intense Raman signals and which can be used as labels for detecting trace quantities of target molecules through conventional techniques. The target for the detection limit utilizing the present compositions and methods is at least as small as the femto-molar level.

1. Signal Molecule

The signal molecule may be any conventionally known signal molecule, including known dyes. Dyes may be any one of those known in the art, such as azo dyes, anthraquinone based dyes, flavonoid dyes, polyphenol dyes, fluorescein derivatives, fluorone dyes, rhodamine dyes, phenylpropanoid dyes, cyanine dyes, polymethine dyes, acridine dyes, phenanthridine dyes, porphyrin dyes, triaryl dyes, oxazin dyes, oxazone dyes and phenoxazine dyes. Specific examples include, but are not limited to, flavonoids, fluorescein, rhodamine, coumarin, cyanine, acridine and their derivatives, including porphyrin derivatives. Additionally, any of the known dyes listed as http://stainsfile.info/StainsFile/dyes/dyes.htm may also be used as a signal molecule according to the present disclosure.

2. Linker

The linkers of the present disclosure may comprise, for example, a molecular group of a predetermined length between the nanoparticle and the signal molecule. The linker group itself may be broken down into two sections. The first section is an organic or inorganic group which is bound, for instance, covalently, to the signal molecule. The second section, which is attached to the organic or inorganic group and is a surface-seeking group.

Examples of organic or inorganic groups include, but are not limited to divalent organic groups such as alkyl, alkenyl, alkynyl, ether, ester, amide, aryl, heteroaryl, or combinations thereof.

These organic or inorganic groups may be optionally substituted with groups such as halogen, cyano, carboxyl, etc.

The surface-seeking group may be a sulfur containing group, such as thiols, disulfides or sulfinates, or polymers having thiol, disulfide, or sulfinate groups. A thiol compound is preferred as a sulfur compound. The thiol compound refers to a general name for an organic compound (R—SH where R represents a hydrocarbon radical such as an alkyl group) containing a mercapto group (—SH).

By way of one embodiment, the linker group may be a series of amino acids. For instance, in one embodiment, the linkers may comprise one cysteine residue at the C-terminus, followed by one or more glycine residues leading to the N-terminus.

In one embodiment, the linker group may be about 4 to about 40 atoms long to provide sufficient exposure. The linker molecules may be, for example, aryl acetylene, ethylene glycol, oligomers containing 2-10 monomer units, diamines, diacids, amino acids, among others, and combinations thereof. Alternatively, the linkers may be polynucleotides, oligopeptides, or oligosaccharides.

The present disclosure allows selection of an appropriate linker group length thereby making it possible to increase the SERRS signal by up to 22 times compared to the SERRS signal achieved without a linker group.

The linker group may serve at least two functions. First, the linker group introduces a 'surface seeking group' that improves the strength of the interaction between the metal nanoparticle and the signal molecule. Second, the linker group holds the signal molecule at an optimal location with respect to the metal nanoparticle surface, providing enhanced SERRS scattering. The combination of these two functions results in a SERRS scattering signal which allows detection limits for the whole SERRS active particle never before achieved.

The present disclosure combines the signal molecule and the linker group. The signal molecule, for example, the chromophore is conjugated to a linker group, such as cysteine. The thiol group of the exemplary linker, cysteine, is used to conjugate the chromophore to a metal nanoparticle. Solid phase synthesis is used to produce chromophores with different length amino acid linkers between the thiol group and the optically active region. By performing these very minor structural changes to the linker group large changes can be seen in the resulting SERRS spectra. These changes in the Raman signal are not predictable by those skilled in the art. For example, upon extending the linker group, one would expect the chromophore to be located further from the metallic surface and so display a reduction in the Raman signal. This was not observed, in fact on the addition of an extra glycine group into the linker region the Raman signal displayed more than a 10 fold increase in signal intensity as compared to the signal without an extra glycine group in the linker.

The present disclosure shows that the systematic modification of a linker group coupling a Raman active chromophore to a SERS active surface is an effective way of enhancing SERRS signals to a level which provides a degree of sensitivity never before achieved. The addition of a single linker unit, such as glycine, has a pronounced effect on the intensity of the overall SERRS response.

3. Particle

The SERRS active particles of the present disclosure are particles to be coated with signal molecules, wherein the signal molecules are modified with the present linker.

For instance, the particles of the present disclosure may be nanoparticles. A "nanoparticle" is a microscopic particle whose size is measured in nanometers. In one embodiment, the nanoparticle has a diameter less than about 200 nm, between about 20 nm and about 200 nm, or between about 40 nm and about 100 nm.

In one embodiment, such nanoparticles are metallic nanoparticles. Such metallic nanoparticles may be non-reactive metals or mixtures of metals such as Au, Cu, Ag. The present nanoparticles may also be conventional particles such as organic or inorganic particles, coated with a metallic coating. For instance, an Au nanoparticle or an Au coated nanoparticle may be used according to the present disclosure.

In one embodiment, the nanoparticle may comprise a metal or a metal alloy, such as gold, silver, copper, nickel, cobalt, iron, palladium, platinum, and aluminum.

According to the present disclosure, nanoparticles are variously defined as materials comprising less than about 10 million atoms, or materials exhibiting a diameter less than about 1,000 nanometers. In certain embodiments, nanoparticles can exhibit diameters less than about 100 nanometers. Nanoparticles may generally be spherical, triangular, rod-like, cubical, vertex-truncated cubical, as well as other shapes, and/or mixtures thereof. Nanoparticles may comprise a single material or multiple materials. For example, nanoparticles may comprise metals such as Au, Ag, Pt, Ni, Co, Ti, Al, Si, Ge, Cu, Cr, W, Fe, Pd, and/or Ir, metal oxides such as metal oxides of any of the foregoing, semiconductors such as group III-V and group II-VI semiconductors such as CdSe, CdS, CdTe, and/or GaAs, organic materials such as polystyrene, HMP-PEGA polyacrylamide, polyacrylic acid, polymethacrylic acid, PEG (Polyethylene glycol), and/or PLGA (Poly(lactic-co-glycolic acid), biological materials such as DNA, proteins, carbohydrates and sugars, and/or composites of any of the foregoing.

4. Analytes/Targets

Targets which may be detected by SERRS are generally proteins, including protein complexes, multimers and derivatives thereof, nucleic acids, carbohydrates and other such molecular substances.

The present disclosure discloses probes which display intense Raman signals and which can be used as labels for detecting trace quantities of target molecules through conventional techniques, such as immunoassays. The target for the detection limit is at least as small as the femto-molar level.

The analyte may be a molecule found directly in a sample such as a body fluid from a host. The sample can be examined directly or may be pretreated to render the analyte more readily detectible. Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay. The body fluid can be, for example, urine, blood, plasma, serum, saliva, semen, stool, sputum, cerebral spinal fluid, tears, mucus, and the like.

Raman spectroscopy-based detection methods can replace the current fluorescence systems and the increased sensitivity provided by the present compositions and methods allows for the detection of low concentration biomarkers, including biomarkers in blood samples. Such low concentration biomarkers may include, but are not limited to, alpha fetoprotein (AFP), γ-aminobutyric acid (GABA), troponin and ADDL. AFP is a glycoprotein normally produced by the fetus during development but also by certain tumors in adults. It can be used to monitor developmental defects in a baby and as a marker for testicular cancer and hepatocellular carcinoma in adults. The normal concentration for AFP in the blood is 0.2 $nM/dm^3$. Troponin is a protein complex found in muscle cells. The presence of Troponin in the blood can be used as a marker for myocardial infarction (heart attacks). The normal concentration for Troponin is 0.02 $nM/dm^3$.

Other embodiments of the present disclosure may be applied to detection of even less concentrated biomarkers. For example, Inhibin, a protein with potential to be a biomarker for ovarian cancer, has a normal concentration in the range of 1.5 $pM/dm^3$. Amyloid-β-Derived Diffusible Ligand (ADDL) is a potential biomarker for Alzheimer's disease and has a normal concentration of only 0.2 $fM/dm^3$. ADDL is undetectable using present techniques and systems. To fully utilize these biomarkers, as well as many others currently under investigation, it is imperative that new immunoassay detection methods are developed that can deliver sub femto-molar and atto-molar detection limits.

The probes of the present disclosure can be used in bioassays and chemical assays as a substitute for conventional fluorescent markers. Instead of viewing the bioassay results with fluorescent microscopes under suitable excitation wavelengths, the results of the present methods are imaged in a desktop Raman device. The peak height or peak area at a particular wavenumber is correlated to the concentration of the target species. The Raman signal from the actual target may be too weak to image; however, the signal from the Raman probes of the present disclosure are $10^{10}$-$10^{18}$ times greater (24). The present labels can be used to label biological species, such as, for example, antibodies, proteins and DNA. These biological species provide the probe the required selectivity, while the Raman signal allows detection of the presence of the biological species. The probes of the present disclosure, and methods of their use, are therefore applicable to many different trace analysis applications and bioassays.

In one embodiment, the bioassay of the present method is a sandwich assay wherein the target is first conjugated to a recognition species, the Raman probe, with a secondary recognition species, which then forms the sandwich structure with the previous conjugate.

EXAMPLES

The present disclosure is exemplified by the following examples. The examples set forth herein are illustrative only and are not intended to in any way limit the scope of the present disclosure.

Example 1

Nanoparticle Synthesis

Experiments herein use a EZRaman-L system spectrometer purchased from Enwave Optronics, operating with 670 nm laser, 22 mW output and a 0.30 NA focusing lens. 5(6) Carboxy-x-rhodamine-N-succinimidyl ester is from Fluka. The solid phase synthesis (SPS) resin, TentaGel S AM, is from Advanced ChemTech.

The Au NPs are synthesised following a citrate reduction method (25, 26, 27). Small Au NPs were made first and used as seed particles to grow the final larger of Au NPs.

The small Au NP seed particles are synthesised by citrate reduction. Trisodium citrate (50 mg) is dissolved in distilled water (5 ml) to produce a 1% solution. This solution is added to a boiling solution of hydrogen tetrachloroaurate (20 mg) in distilled water (50 mL). The resulting solution changes color to give a deep red/purple. The heat is removed after refluxing for 30 minutes.

Figure 2:
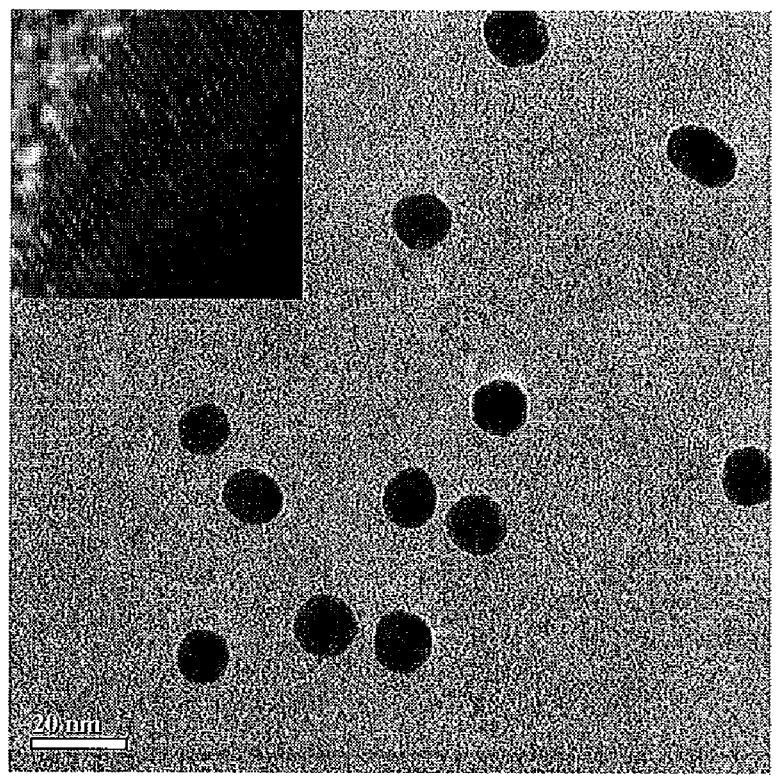
FIG. 2: TEM images of small seed Au nanoparticles. The inset shows a single nanoparticle, with an image width of 5 nm.

The UV-Vis spectrum for the solution was recorded from 300 nm to 900 nm and showed the characteristic surface plasmon resonance peak at wavelength 517 nm. TEM image analysis gave a NP diameter of 12.2±0.8 nm. A representative TEM image is depicted in FIG. 2. The inset shows a close-up of a single Au NP showing the lattice structure.

The large Au NP are synthesised by seed particle growth with citrate reduction. Hydrogen tetrachloroaurate solution (0.5 mL, 11 mM solution) is added to distilled water (32 mL) and brought to reflux with a fitted condenser. The seed solution from the above small Au NP synthesis is added to this (0.3 mL), followed closely by trisodium citrate solution (0.17 mL of 1% solution). The solution changes to a blue color after 30 sec and a red color after 1 minute. After 10 minutes the heat is removed and the solution allowed to cool with stirring.

Figure 3:
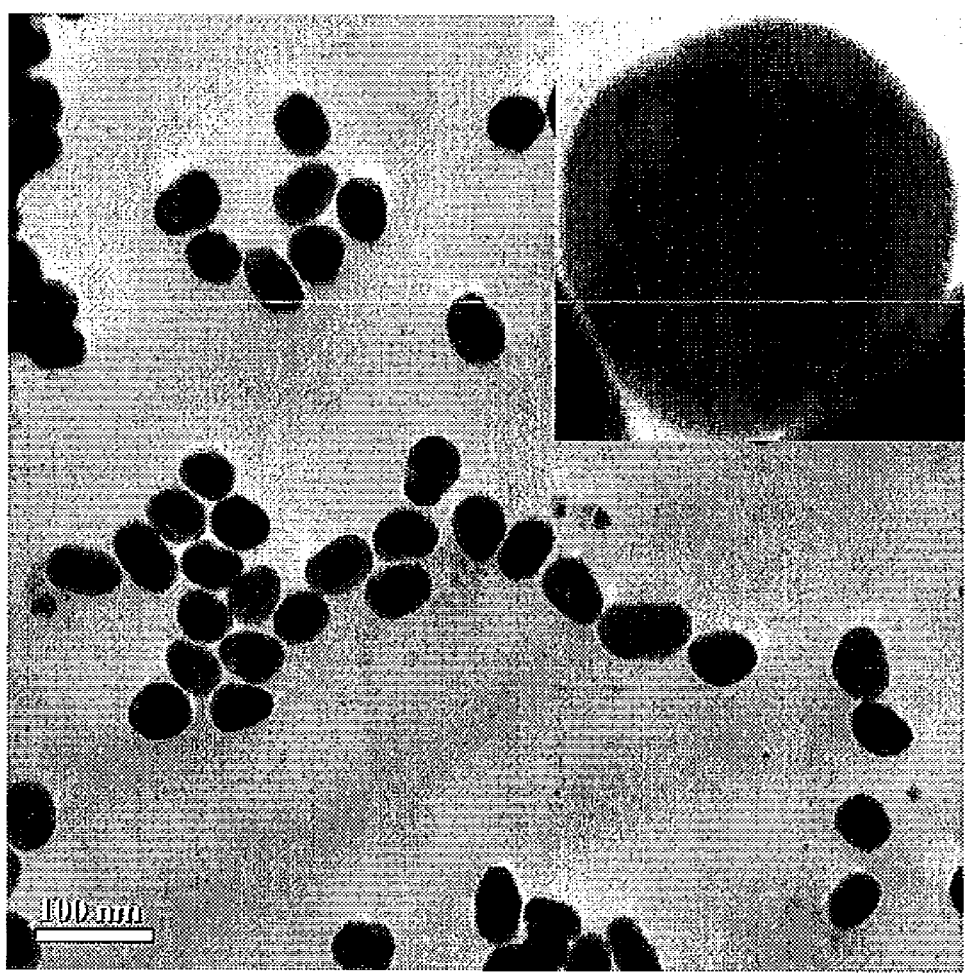
FIG. 3: TEM images of large Au nanoparticles. The inset shows a single nanoparticle, with an image width of 50 nm.

The UV-Vis spectrum for the solution was recorded from 300 nm to 900 nm and showed the characteristic surface plasmon resonance peak at wavelength 535 nm. TEM image analysis gives a NP diameter of 49.8±1.2 nm. A representative TEM image is depicted in FIG. 3. The inset of FIG. 3 shows a close-up of a single Au NP.

Example 2

Preparation of Fmoc-Cys(Trt) Loaded TentaGel S AM Resin (1a)

The solid phase synthesis (SPS) resin (SJ5075 Advanced Chemtech) is first activated by removal of the Fmoc protecting group (28). Typically, the resin (2 g) is suspended in a solution of 20% piperidine 80% DMF (20 mL) with agitation for approximately 30 minutes. The solution is removed and the resin washed three times with fresh piperidine/DMF solutions. The UV-Vis spectrum is observed to monitor the release of the Fmoc group.

Once activated, the Fmoc-Cys(Trt)-OH amino acid is coupled to the resin following standard benzotriazol-1-yl-oxytripyrrolidino-phosphonium hexafluorophosphate (PyBOP) conditions. Fmoc-Cys(Trt)-OH (0.36 g) and PyBOP (0.30 g) are dissolved in DMF (20 mL) and DIPEA (200 µL) is added. The activated resin (2 g) is then added and the whole solution is agitated mildly for 24 hours at room temperature. After this time, the resin is washed three times with fresh DMF, then three times with ethanol and then dried to constant mass under vacuum.

The success of the reaction is determined by a subsequent Fmoc assay. As expected, no obvious color change is observed during the amino acid coupling reaction. The loading of the Fmoc-Cys(Trt) is calculated to be 0.13 mmolg$^{-1}$.

Example 3

Preparation of Fmoc-Gly-Cys(Trt) Loaded TentaGel S AM Resin (2a)

Fmoc-Cys(Trt) loaded TentaGel S AM resin as synthesized above is first activated by removal of the Fmoc protecting group. Typically, the resin (2 g) is suspended in a solution of 20% piperidine 80% DMF (20 mL) with agitation for approximately 30 minutes. The solution is removed and the resin washed three times with fresh piperidine/DMF solutions. The UV-Vis spectrum is observed to monitor the release of the Fmoc group.

Once activated, the Fmoc-Gly-OH amino acid is coupled to the resin following standard PyBOP conditions. Fmoc-Gly-OH (0.1 g) and PyBOP (0.15 g) are dissolved in DMF (20 mL) and DIPEA (150 µL) is added. The activated resin (2 g) is then added and the whole solution is agitated mildly for 24 hours at room temperature. After this time, the resin is washed three times with fresh DMF, then three times with ethanol and then dried to constant mass under vacuum. The success of the reaction is determined by a subsequent Fmoc assay. As expected, no obvious color change are observed during the amino acid coupling reaction. The loading of the Fmoc-Gly-Cys(Trt) was calculated to be 0.12 mmolg$^{-1}$.

Example 4

Preparation of Fmoc-Gly-Gly-Cys(Trt) Loaded TentaGel S AM Resin (3a)

Fmoc-Gly-Cys(Trt) loaded TentaGel S AM resin as synthesized above is first activated by removal of the Fmoc protecting group. Typically, the resin (1 g) is suspended in a solution of 20% piperidine 80% DMF (20 mL) with agitation for approximately 30 minutes. The solution is removed and the resin is washed three times with fresh piperidine/DMF solutions. The UV-Vis spectrum is observed to monitor the release of the Fmoc group.

Once activated, the Fmoc-Gly-OH amino acid is coupled to the resin following standard PyBOP conditions. Fmoc-Gly-OH (0.05 g) and PyBOP (0.08 g) are dissolved in DMF (10 mL), and then DIPEA (75 μL) is added. The activated resin (1 g) is then added and the whole solution is agitated mildly for 24 hours at room temperature. After this time the resin is washed three times with fresh DMF, then three times with ethanol and then dried to constant mass under vacuum. The success of the reaction is determined by a subsequent Fmoc assay.

As expected, no obvious color change is observed during the amino acid coupling reaction. The loading of the Fmoc-Gly-Gly-Cys(Trt) was calculated to be 0.10 mmolg$^{-1}$.

Example 5

Carboxy-x-rhodamine-N-succinimidyl Ester Coupling (1b, 2b and 3b)

This synthesis is performed using standard conditions with bicarbonate buffer. The buffer is made fresh by titrating a mixture of 0.5M NaCl and 0.1M NaHCO$_3$ (20 ml total volume) with a mixture of 0.5M NaCl and 0.1M Na$_2$CO$_3$ to yield a solution having a pH of 8.3. Briefly, the loaded resins as prepared above are activated by removal of the Fmoc protecting group. Typically, the resin (1 mg) is suspended in a solution of 20% piperidine 80% DMF (0.5 mL) with agitation for approximately 30 minutes. The solution is removed and the resin washed three times with fresh piperidine/DMF solutions. The UV-Vis spectrum is observed to monitor the release of the Fmoc group.

The resin is then extensively washed with ethanol until no trace of piperidine is found. Afterwards, the resin is further washed three times with distilled water. The resin is then dispersed in the bicarbonate buffer solution (0.3 mL). Carboxy-x-rhodamine-N-succinimidyl ester (7.5 mg) is dissolved in DMF (100 μL). 25 μL aliquots of this solution are then added to each of the resin/bicarbonate mixtures. The final mixtures are then agitated in a dark environment over night. The resin is then washed several times with ethanol until no color is observed in the wash solution.

As expected, the resin turns from an initial yellow brown color, to a pink/red color following the carboxy-x-rhodamine coupling reaction.

Example 6

Thiol Deprotection and Trt Assay

The Trt protecting group on the Cys thiol is removed by washing with 10% TFA/DCM. The strong UV-Vis adsorption of the Trt$^+$ cation is used to estimate the amount of Cys loaded onto the resin. The loaded resins with carboxy-x-rhodamine label (1 mg) are carefully washed with ethanol, acetone and DCM to remove any unbound dye. The resins are then suspended in a 10% TFA/90% DCM solution (1 mL) for 20 minutes. Afterwards, the solution is removed and stored in a sealed container. This is repeated until the TFA/DCM solution no longer turns yellow on exposure to the resin. The TFA/DCM washings are then combined and diluted to 5 mL with fresh TFA/DCM. The UV-Vis spectrum of the solution is then recorded.

The trityl cation has a strong absorption in the visible spectrum at λ=410 nm, extinction coefficient 37555 mol$^{-1}$dm$^3$cm$^{-1}$. The trityl assay yields a value for the Cys loading of 0.10 mmol/g for all three resins, which is in good agreement with the initial Fmoc loading. The presence of the thiol group may be further confirmed by a positive Ellman test (29).

Example 7

Product Recovery

The three products, carboxy-x-rhodamine-Cys(SH) (1c), carboxy-x-rhodamine-Gly-Cys(SH) (2c) and carboxy-x-rhodamine-Gly-Gly-Cys(SH) (3c), are removed from the SPS resin by washing with 90% TFA/DCM. The loaded resin (1 mg) is suspended in 90% TFA/DCM (1 mL) for 30 minutes with agitation. Afterwards, the solution is removed and stored in a sealed container. This is repeated three times, with the final washing being 100% TFA. The TFA extracts are then combined and the solvent removed by rotary evaporation under reduced pressure and at 50° C., leaving a pink/purple residue.

The residue is dissolved in distilled water (200 μL) to give the expected pink/purple solution. The control product with no dye label is recovered in the same manner, but results in a colorless residue.

Before and after each coupling reaction, the resin is tested for amine groups using a standard Kaiser test. The concentration of the final products is estimated from UV-Vis spectroscopy of the final aqueous solution, assuming that the modified carboxy-x-rhodamine has the same extinction coefficient as the initial carboxy-x-rhodamine label ($\epsilon_{580}$=8085.5 mol$^{-1}$dm$^3$cm$^{-1}$). These products have a strong absorption in the visible spectrum at λ=580 nm, which is identical to the carboxy-x-rhodamine starting material. The presence of the thiol group is confirmed by a positive Ellman test. The structure of the three products can be seen in FIG. 1.

The nanoparticle synthesis is based on the growth of a small seed particle to form larger particles. These larger particles display an increased SERS enhancement factor as compared to the initial seed particles. TEM images of both the seed particles and the larger final particles can be seen in FIG. 2 and FIG. 3, respectively. Image analysis reveals an average particle diameter of 12.2±0.8 nm and 49.8±1.2 nm, respectively. During the growth stage the peak maximum for the Au surface plasmon resonance shifts from 517 nm to 539 nm and the color of the nanoparticle solution changes from a deep red to a more purple color. The final nanoparticle solution is very stable and shows only slight sedimentation over a period of several days. The solution is readily dispersed with no loss observed in the UV-Vis spectra.

Example 8

SERRS Signal Collection

The SERRS signal is recorded using a EZRaman-L system purchased from Enwave Optronics operating with 670 nm laser, 22 mW out put and a 0.30 NA focusing lens. The product (2 μL) is mixed with a solution of the large Au NPs (100 μL) and distilled water (398 μL) in a 1.5 mL sample vial. The sample vial is mixed briefly with sonication and placed in the spectrometer sample holder. The sample holder, from Enwave Optronics, arranges the sample vial and excitation laser in an optimal orientation so that the focus point of the laser is located at the center of the 1.5 mL vial, 2 mm from the base of the vial. The integration time used to collect the SERRS spectra often varies; however, the most common setting is for 10 seconds.

The SERRS spectra for the three products were recorded by adding 2 μL of the product solution to a 100 μL of the large Au NP solution and diluting the mixture to 0.5 mL with distilled water. The final solution is placed in a sample vial located in the sample holder. The holder holds the sample so that the laser focus point falls in the centre of the solution. The laser exits the 105 μm diameter waveguide and passes through a collimation lens, giving a beam width of 0.25 cm. The beam then passes through a lens with a focus length of 0.7 cm, giving a spot diameter of 100 μm at is focus point.

With this set-up, the laser effectively illuminates and collects a signal from a volume of 6.9 nL within the sample. The intensity of the SERRS signal is dependent on two factors, the concentration of the Raman active dye (1c, 2c or 3c, see FIG. 1) and the integration time for the signal processing.

To compensate for these two variables, the SERRS spectra are plotted as a function of the scattering coefficient ($S_c$). $S_c$ has the units of $mol^{-1}$ $dm^{-3}$ and is defined as the Raman signal intensity (I) divided by both the concentration (C) of the Raman dye in mol $dm^{-3}$ and by the integration time (t) in seconds, $S_c = I/(C \times t)$. It can be seen in FIG. 4 that the spectra of the modified Raman dye 2c is very similar to that of the unmodified Carboxy-x-rhodamine. Peaks associated with the C—C aromatic stretch are dominant in both samples at 1346 $cm^{-1}$, 1503 $cm^{-1}$ and 1647 $cm^{-1}$. These are consistent with other published values for rhodamine aromatic systems (30).

Figure 4:
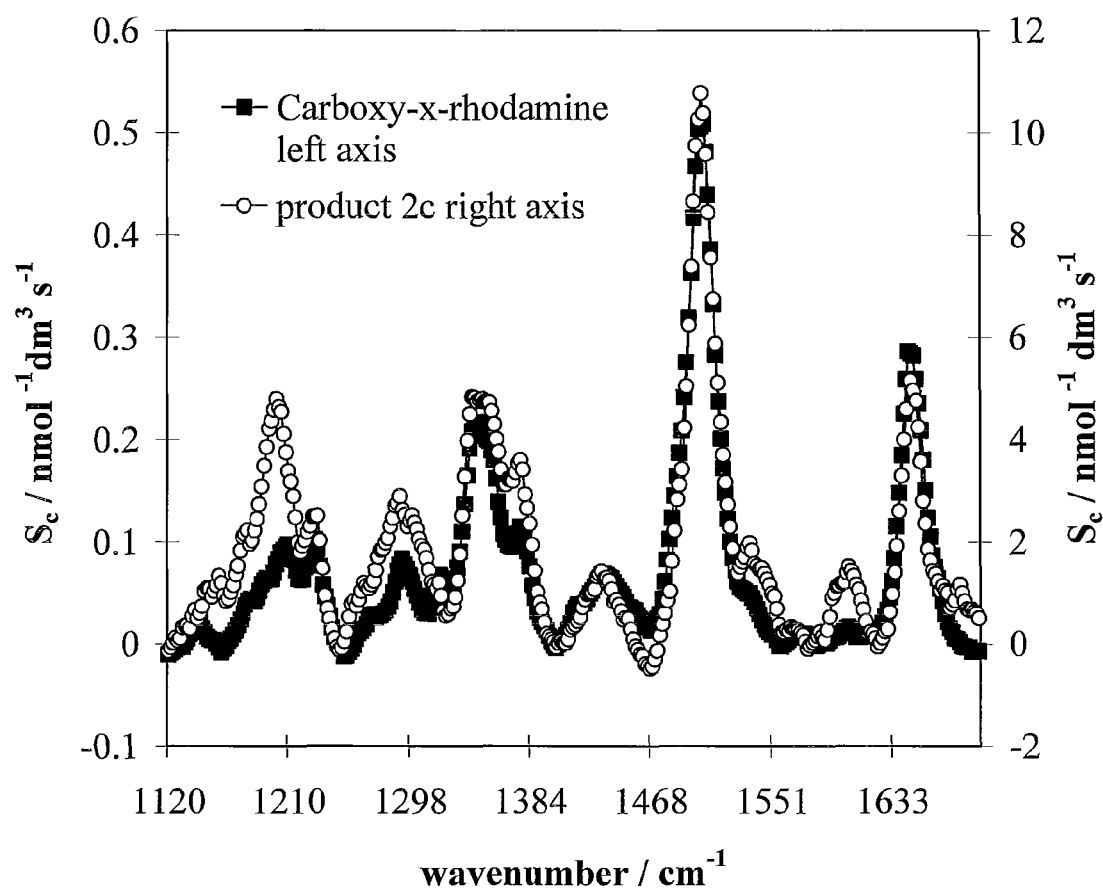
FIG. 4: Raman spectra overlay showing the difference between 2c and the unmodified carboxy-x-rhodamine.

The modified dye 2c shows increased peak intensity at 1203 $cm^{-1}$ and 1291 $cm^{-1}$. These are assigned to the C—N stretch of the peptide bond and are consistent with the proposed structure (31, 32). The interesting feature observed in FIG. 4 is the increased intensity of all the bands, particularly the C—C aromatic stretch at 1503 $cm^{-1}$. The Scattering coefficient ($S_c$) for this band is about 22 times greater for product 2c as compared to the standard carboxy-x-rhodamine dye with values of 11 $mol^{-1}$ $dm^3$ $s^{-1}$ and 0.5 $mol^{-1}$ $dm^3$ $s^{-1}$, respectively.

Conventional SERS theory predicts that the signal intensity will be proportional to the coverage of the Raman dye on the surface of Au NPs. Adding a surface seeking group, such as a thiol, to the dye structure results in an increased signal. The thiol group has a strong chemical bond to the gold surface, resulting in a shift in the equilibrium between bound and unbound dye molecules, and leading to an increase in surface density. This is consistent with experimental observations.

Figure 5:
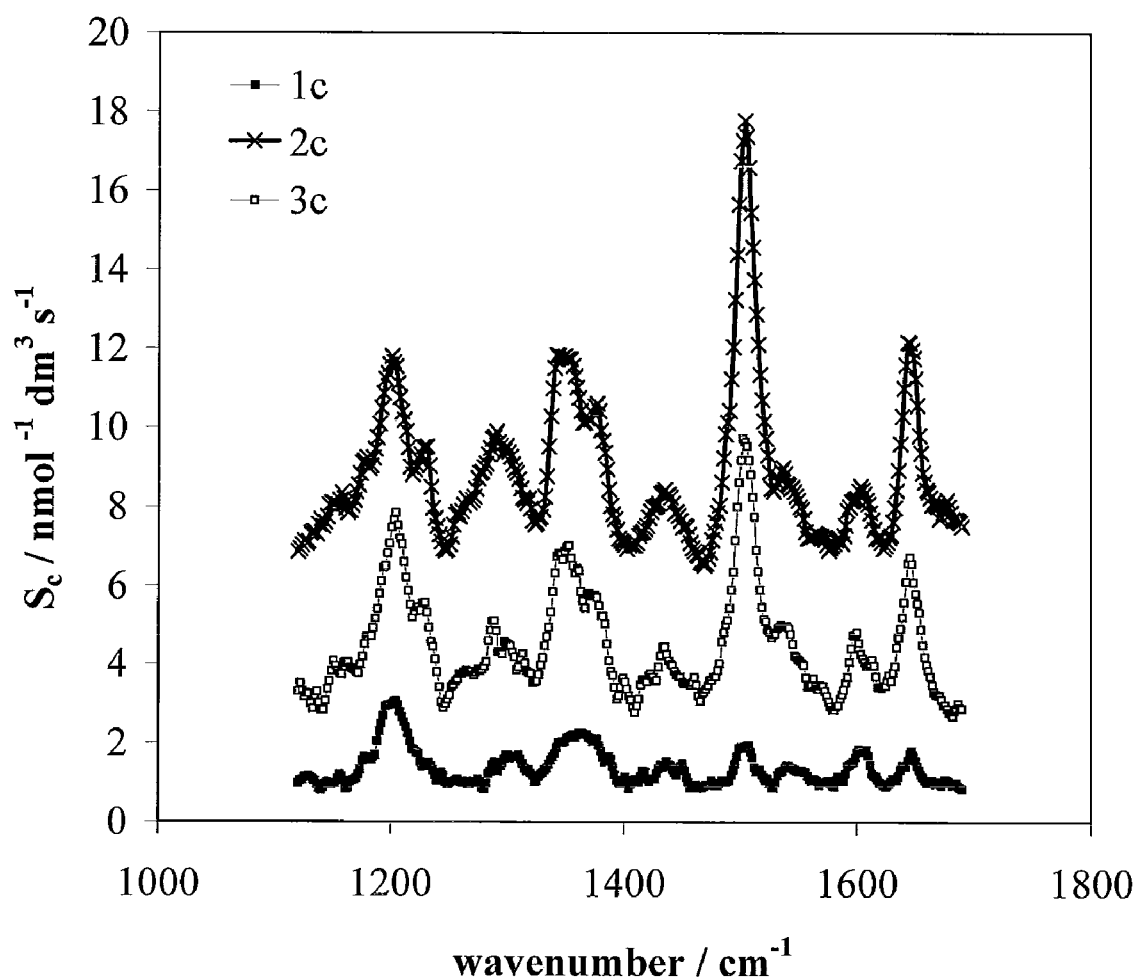
FIG. 5: Raman spectra overlay showing the difference signal intensity of 1c, 2c and 3c. The spectra are offset from zero for ease of viewing.

However this theory cannot explain the difference in signal intensity between the three modified dyes 1c, 2c and 3c. The Raman spectra for these three dyes can be seen in FIG. 5. The spectra are offset slightly for easy of view. It can be seen from this that product 2c has the most intense signal at 1503 $cm^{-1}$. Product 1c has the weakest signal, although this weaker signal is still twice as strong as the unmodified dye. The $S_c$ value for the 1503 $cm^{-1}$ peak associated with 1c and the unmodified dye are 1 $mol^{-1}$ $dm^3$ $s^{-1}$ and 0.5 $mol^{-1}$ $dm^3$ $s^{-1}$, respectively. Product 3c has a $S_c$ value of 7 $mol^{-1}$ $dm^3$ $s^{-1}$, which is roughly 14 times that of the unmodified dye.

As all three of the products 1c, 2c and 3c have the same surface seeking group bonding to the Au NP surface, and differ in chemical structure by the addition of a glycine unit, the contribution to the Raman signal from the chemical enhancement should be roughly equal. The contribution from the surface enhancement should be the same for all three products. If the linker group, the peptide chain, is considered to be a rigid support of limited flexibility, then the Raman active chromophore is placed at a set distance from the Au NP surface, the distance increasing in the range 1c, 2c, 3c. This increased distance from the surface results in a reduction in the Raman signal as the field intensity decays. However, the linker groups are not necessarily rigid supports. As the extra glycine units are added to the peptide chain, the chain becomes more flexible allowing increased mobility of the rhodamine chromophore. This increased mobility is believed to allow the chromophore to exist in different orientations with respect to the Au NP surface.

The overall SERRS enhancement depends on a number of different mechanisms and the orientation of the chromophore to the SERS surface is one of these factors (33). As the extra glycine units are placed in the linker group there are two competing mechanisms for the SERRS enhancement, the decreasing signal intensity due to increased distance from the Au NP surface and an increase in signal intensity due to the re-orientation of the chromophore. In this system, the optimal linker group is the dipeptide 2c composed of Cys-Gly. The inclusion of a second glycine unit to give 3c results in an overall decrease in the Raman signal intensity.

Example 9

Preparation of Atto680 Probes

The SERRS spectra of three modified atto680 dyes were recorded using Au nanoparticles and an excitation laser operating at 670 nm. The dyes were modified with linker groups based on the small peptides, Cys, Cys-Gly and Cys-Gly-Gly. The Cys thiol group acted as the coupling point to the Au surface and the Gly-$NH_2$ group used to attach the dye. The maximum signal was recorded for the Cys-Gly linker. This gave a signal intensity for the 577 $cm^{-1}$ Raman peak of the atto680 dye that was more than 27 times greater than the unmodified dye. The Au nanoparticles used had a diameter of 49.8±1.2 nm and were synthesised by the citrate reduction method. The Raman dye-AuNP probes were also used in an immunoassay to detect 1 femto mole of mouse IgG.

The desktop Raman spectrometer was an EZRaman-L system purchased from Enwave Optronics operating with 670 nm laser, 22 mW measured output and a 0.30 NA focusing lens. Atto680-N-succinimidyl ester was purchased from Fluka, the solid phase synthesis (SPS) resin, TentaGel S AM, was purchased from Advanced ChemTech.

Nanoparticles, small AuNP seed particles, and large AuNP were prepared as in Example 1. Further, Fmoc-Cys(Trt) loaded TentaGel S AM resin (1a), Fmoc-Gly-Cys(Trt) loaded TentaGel S AM resin (2a) and Fmoc-Gly-Gly-Cys(Trt) loaded TentaGel S AM resin (3a) were prepared as in Examples 2, 3 and 4, respectively.

Atto680-N-succinimidyl ester (1d, 2d and 3d) coupling was performed using standard conditions with bicarbonate buffer. The buffer was made fresh each day by titrating a mixture of 0.5M NaCl and 0.1M $NaHCO_3$ (20 ml total volume) with a mixture of 0.5M NaCl and 0.1M $Na_2CO_3$ to give pH 8.3. Briefly the loaded resins as prepared above were activated by removal of the Fmoc protecting group. The resin was then extensively washed with ethanol until no trace of piperidine could be found. After this the resin was further washed three times with distilled water. The resin was then dispersed in the bicarbonate buffer solution (0.3 mL). Atto680-N-succinimidyl ester (1 mg) was dissolved in DMSO (500 μL) and aliquots of this were added to each of the resin/bicarbonate mixtures to give a final concentration of 2 mg $ml^{-1}$ with respect to the dye. The final mixtures were then left with agitation in a dark environment over night. The resins were washed several times with ethanol until no colour could be observed in the wash solution. As expected the resin turned from an initial yellow brown colour to a green colour following atto680 coupling.

Example 10

Thiol Deprotection and Trt Assay

The Trt protecting group on the Cys thiol was removed by washing with 10% TFA/DCM. The strong UV-Vis adsorption of the Trt$^+$ cation was used to estimate the amount of Cys loaded onto the resin. The loaded resins complete with dye (1 mg) were carefully washed with ethanol, acetone and DCM to remove any unbound dye. The resins were then suspended in 10% TFA 90% DCM solution (1 mL) for 20 minutes. After this time the solution was removed and stored in a sealed container. This was repeated until the TFA/DCM solution no longer turned yellow on exposure to the resin. The TFA/DCM washings were then combined and diluted to 5 mL with fresh TFA/DCM. The UV-Vis spectrum of the solution was then recorded. The trityl cation has a strong absorption in the visible spectrum at $\lambda=410$ nm, extinction coefficient 37555 mol$^{-1}$ dm$^3$ cm$^{-3}$. The trityl assay gave a value for the Cys loading of 0.10 to 0.12 mmol g$^{-1}$ for all the resins, in good agreement with the initial Fmoc loading. The presence of the thiol group was further confirmed by a positive Ellman test (29).

Example 11

Product Recovery

The products, atto-Cys(SH) (1e), atto-Gly-Cys(SH) (2e) and atto-Gly-Gly-Cys(SH) (3e) were removed from the SPS resin by washing with 90% TFA/DCM. The loaded resin (1 mg) was suspended in 90% TFA/DCM (1 mL) for 30 minutes with agitation. After this time the solution was removed and stored in a sealed container. This was repeated three times with the final washing being 100% TFA. The TFA extracts were combined and the solvent removed by rotary evaporation under reduced pressure and 50° C. leaving a blue residue for the atto based dyes. The residue was dissolved in distilled water (500 µL). The control product with no dye label was recovered in the same way but resulted in a colourless residue.

Example 12

SERRS Spectra

The SERRS spectra for the products were recorded by adding 0.5 mL of the product solution to 200 µL of the large AuNP solution. Initially the solution had a strong fluorescence signal masking the SERRS spectra. The solutions were left for 48 hours allowing the AuNPs to settle out. After this time the liquid was decanted off and the NPs redispersed in 1.2 ml of water. After redispersion the solution was centrifuged at 12000 rpm for 10 minutes and the solution decanted again and redispersed in 1.2 ml of fresh water. The cleaning process was repeated 5 times. The final solution was placed in a sample vial located in the sample holder of the SERRS set-up.

Example 13

Immunoassay

The AuNPs modified with 2e and used for the SERRS detection were coated with goat derived anti-mouse IgG $F_{ab}$. Briefly the AuNP solution (500 µl) was mixed with 5 µl of aqueous EDC (7 mg ml$^{-1}$) and 5 µl of anti mouse IgG (90 µg ml$^{-1}$) and left mixing over night. A second AuNP label composed of 4-mercaptobenzoic acid (MBA) coat AuNPs was also synthesised. For this the large AuNPs as synthesised were mixed with MBA (50 mg) dissolved in 5 ml of ammonia (1 moldm$^{-3}$). These were coated with goat derived anti-mouse IgG $F_{ab}$ as before. For the capture antibody gold coated glass slides were first activated with the homobifunctional cross linker-3,3'-dithiobis[sulfosuccinimidylpropionate] (DTSSP). The gold coated slides were sonicated for 5 minutes then DTSSP (0.6 mg) dissolved in distilled water (100 µl) was placed over a 1 cm$^{-2}$ area on the gold surface, three areas were used per slide. After 24 hours the slides were washed with DI water and 28 µl of a solution of rabbit derived anti-mouse IgG $F_c$ (90 µgml$^{-1}$) in borate buffer (50 mM) was placed over the same area. The slides were stored at 4° C. for 24 hours. After coating the substrate was rinsed with DI water, dried and finally exposed to 100 µl of SuperBlock buffer for 30 minutes. Different concentrations of mouse IgG (100 µl) were placed over two of the three 1 cm$^{-2}$ areas, these were 40 µgml$^{-1}$, 20 µgml$^{-1}$ respectively, the third area was used as a blank control and not exposed to mouse IgG. The three areas were then exposed to 100 ul of the AuNP labels coated with anti mouse IgG, washed with DI water and dried. The SERRS spectrum was recorded from the surface. The same procedure was repeated for the MBA-AuNP labels.

Figure 6:
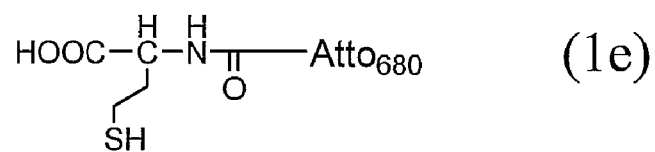
FIG. 6: The structure of the three modified atto680 dyes.
Figure 6:
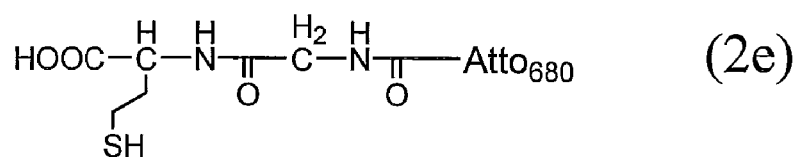
Figure 6:
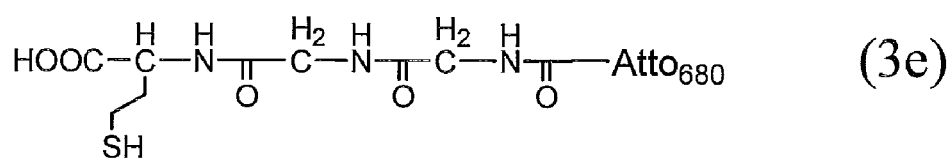

The synthesis of the atto680 dye amino acid sequences proceeded as expected. Before and after each coupling reaction the resins were tested for amine groups using a standard Kaiser test. The concentration of the final products was estimated from UV-vis spectroscopy of the final aqueous solution assuming that the modified dye had the same extinction coefficient as the initial dye label ($\epsilon_{680}=157143$ mol$^{-1}$ dm$^3$ cm$^{-1}$ for atto680). The product has a strong absorption in the visible spectrum at $\lambda=680$ nm identical to the starting material. The presence of the thiol group was confirmed by a positive Ellman test. The structure of the three products can be seen in FIG. 6. The nanoparticle synthesis was based on the growth of small seed particles to form larger particles. These larger particles displayed an increased SERS enhancement factor compared to the initial seed particles. TEM images of both the seed particles and the larger final particles can be seen in FIGS. 2 and 3, respectively. Image analysis revealed an average particle diameter of 12.2±0.8 nm and 49.8±1.2 nm. During the growth stage the peak maximum for the Au surface plasmon resonance shifted from 517 nm to 539 nm and the colour of the nanoparticle solution changed from a deep red to a more purple colour. The final nanoparticle solution was very stable and showed only slight sedimentation over a period of several days. The solution could be readily dispersed with no loss observed in the UV-Vis spectra.

Figure 7:
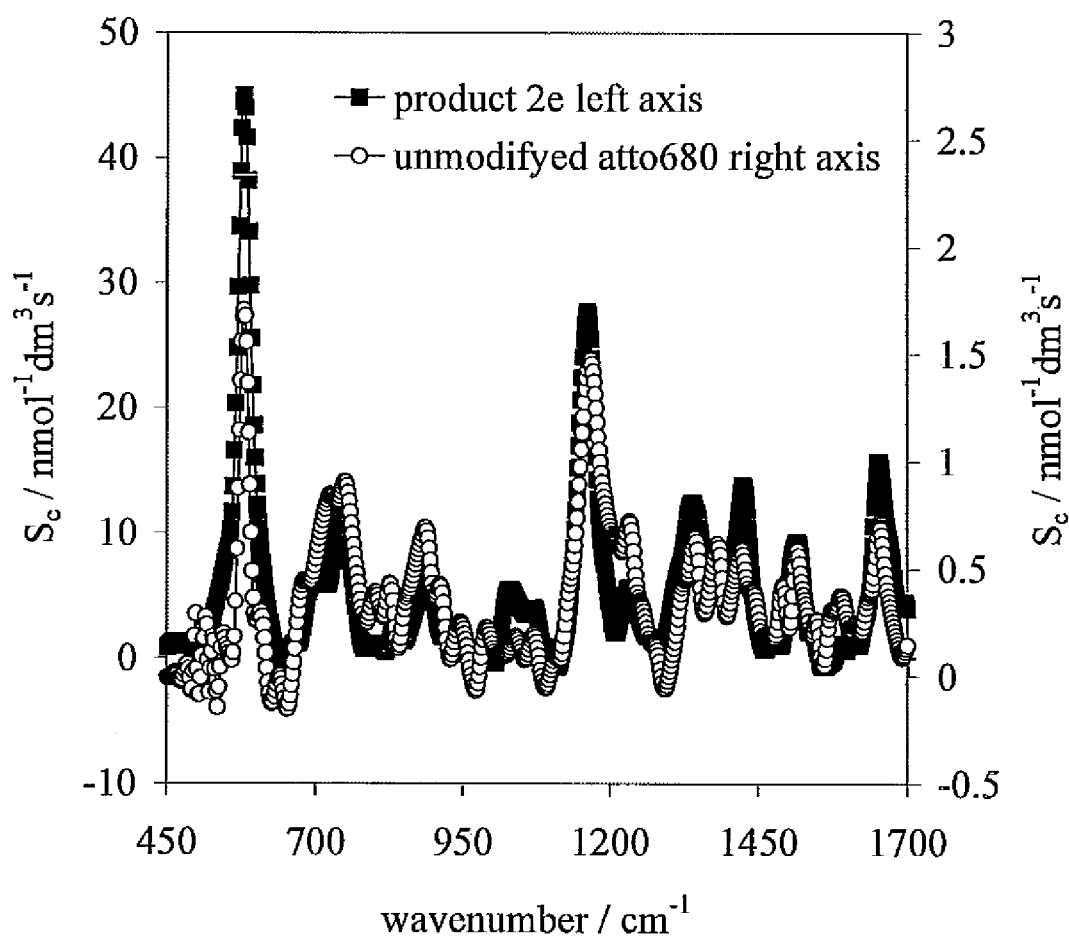
FIG. 7: Raman spectra overlay showing the difference between 2e and the unmodified atto680.

The SERRS spectra of the samples were recoded using the desk-top system. The final solution (1.2 ml) was placed in the sample holder. The holder held the sample so that the laser focus point fell in the centre of the solution. The laser exits the 105 µm diameter waveguide and passes through a collimation lens giving a beam width of 0.25 cm. The beam then passes through a lens with a focus length of 0.7 cm giving a spot diameter of 100 µm at is focus point. With this set-up the laser effectively illuminates and collects a signal from a volume of 6.9 nL within the sample. The intensity of the SERRS signal is dependent on two factors, the concentration of the Raman active dye and the integration time for the signal processing. In order to compensate for these two variables the SERRS spectra is plotted as a function of the scattering coefficient ($S_c$). $S_c$ has the units of mol$^{-1}$ dm$^3$ s$^{-4}$ and is defined as the Raman signal intensity (I) divided by both the concentration (C) of the Raman dye in mol dm$^{-3}$ and by the integration time (t) in seconds, $S_c=I/(C\times t)$. It can be seen in FIG. 7 that the spectra of the modified Raman dye 2e is very similar to that of the unmodified atto680 dye. The structure of Atto680 is proprietary and so unknown; however, it is believed to be a benzophenoxazine based dye (34). The Raman spectrum is similar to that of the benzophenoxazine dye Nile Blue (35). Peaks associated with the C—C skeletal deformation modes and the C—O—C, C—N—C modes are dominant at 577 cm$^{-1}$, 1160 cm$^{-1}$ and 1230 cm$^{-1}$ respectively. The modified dye 2e shows increased peak intensity at 1203 cm$^{-1}$ and 1291 cm$^{-1}$ these can be assigned to the C—N stretch of the peptide bond and is consistent with the proposed structure (31,32). The interesting feature of FIG. 7 is the increased intensity of all the bands, particularly the C—C skeletal deformation modes at 577 cm$^{-1}$. The Scattering coefficient ($S_c$) for this band is about 27 times greater for product 2e compared to the standard atto680 dye with values of 45 nmol$^{-1}$ dm$^3$ s$^{-1}$ and 1.7 nmol$^{-1}$ dm$^3$ s$^{-1}$ respectively. Conventional SERS theory predicts that the signal intensity will be proportional to the coverage of the Raman dye on the surface of AuNPs. Adding a surface-seeking group, such as a thiol, to the dye structure will result in an increased signal. The thiol group has a strong chemical bond to the gold surface leading to an increase in surface density. However this theory alone cannot be used to explain the difference in signal intensity between the three modified dyes 1e, 2e and 3e. The Raman spectra for these dyes can be seen in FIG. 8.

Figure 8:
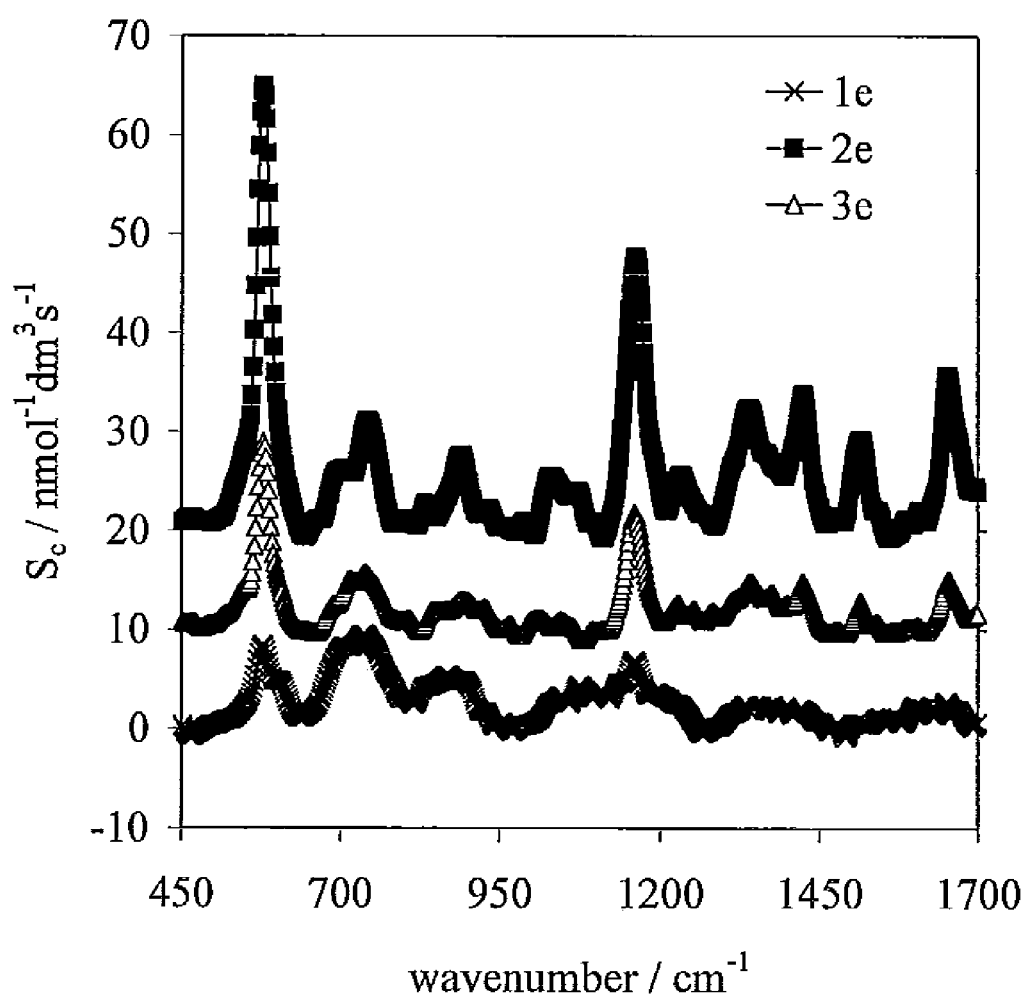
FIG. 8: Raman spectra overlay showing the difference signal intensity of 1e, 2e and 3e. The spectra have been offset from zero for ease of viewing.

In FIG. 8 the spectra are offset slightly for easy of view. It can be seen from this that product 2e has the most intense signal at 577 cm$^{-1}$ and product 1e has the weakest signal, however this is still five times as strong as the unmodified dye. The $S_c$ value for the 577 cm$^{-1}$ peak associated with 1e and the unmodified dye are 8.3 nmol$^{-1}$ dm$^3$ s$^{-1}$ and 1.7 nmol$^{-1}$ dm$^3$ s$^{-1}$ respectively. Product 3e has a $S_c$ value of 18.5 nmol$^{-1}$ dm$^3$ s$^{-1}$ roughly 11 times that of the unmodified dye. As all three of the products 1e, 2e and 3e have the same surface-seeking group bonding to the AuNP surface and only differ in chemical structure by the addition of a glycine unit the contribution to the Raman signal from the chemical enhancement should be roughly equal, also the contribution from the AuNP surface enhancement should be the same for all three products. If the linker group, the peptide chain, is considered to be a rigid support of limited flexibility then the Raman active chromophore would be placed at a set distance from the AuNP surface, the distance increasing in the range 1e, 2e, 3e. This increased distance from the surface would result in a reduction in the Raman signal as the optical field intensity decays. However the linker groups are not rigid supports. As the extra glycine units are added to the peptide chain the chain becomes more flexible allowing increased mobility of the atto680 chromophore. This increased mobility allows the chromophore to take-up different orientations with respect to the AuNP surface.

The overall SERRS enhancement is known to depend on a number of different mechanisms and the orientation of the chromophore to the SERS surface is one of these factors (36). As the extra glycine units are placed in the linker group there are two competing mechanism for the SERRS enhancement, the decreasing signal intensity due to increased distance from the AuNP surface and an increase in signal intensity due to the re-orientation of the chromophore. In this system the optimal linker group is the di-peptide used in 2e this is composed of Cys-Gly. The inclusion of a second glycine unit to give 3e results in an overall decrease in the Raman signal intensity.

The modification of a chromophore with a surface seeking group such as a thiol has been well documented and the distance dependence of the SERS surface has also been heavily investigated but to our knowledge the combination of both a spacer group and a surface seeking ligand all covalently coupled to the dye and the NP surface has not been documented. This work shows that the systematic modification of a linker group coupling a Raman active chromophore to a SERS active surface can be an effective way of optimising SERRS signals and that the addition of a single glycine unit can have a pronounced effect on the intensity of the overall SERRS response. By selecting the appropriate linker group it is possible to increase the SERRS signal from the atto680-AuNP probe by up to 27 times. For comparison Kennedy et al. observed a 3-fold drop in the SERS signal when going from a C8 spacer to a C18 spacer (37).

Figure 9:
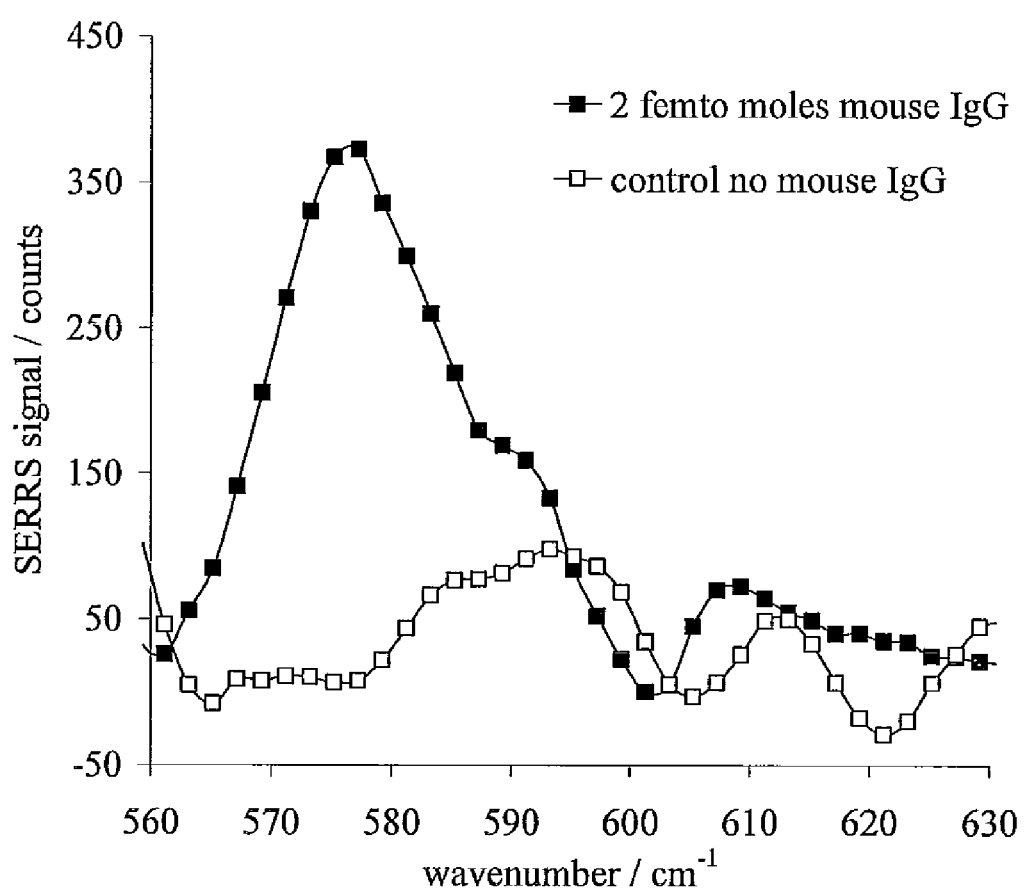
FIG. 9: SERRS signal collected from the surface of the slide after running the immunoassay using 2e modified AuNPs as the label.
Figure 10:
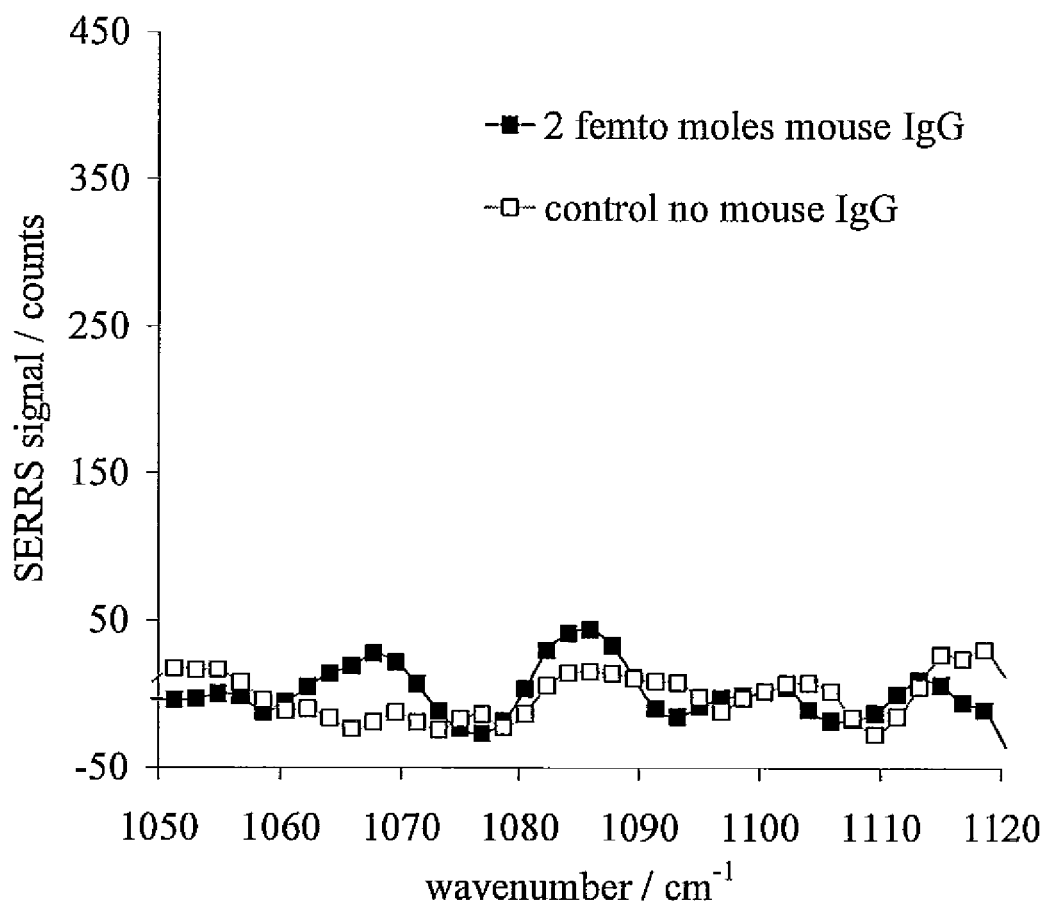
FIG. 10: SERRS signal collected from the surface of the slide after running the immunoassay using MBA modified AuNPs as the label.
Figure 11:
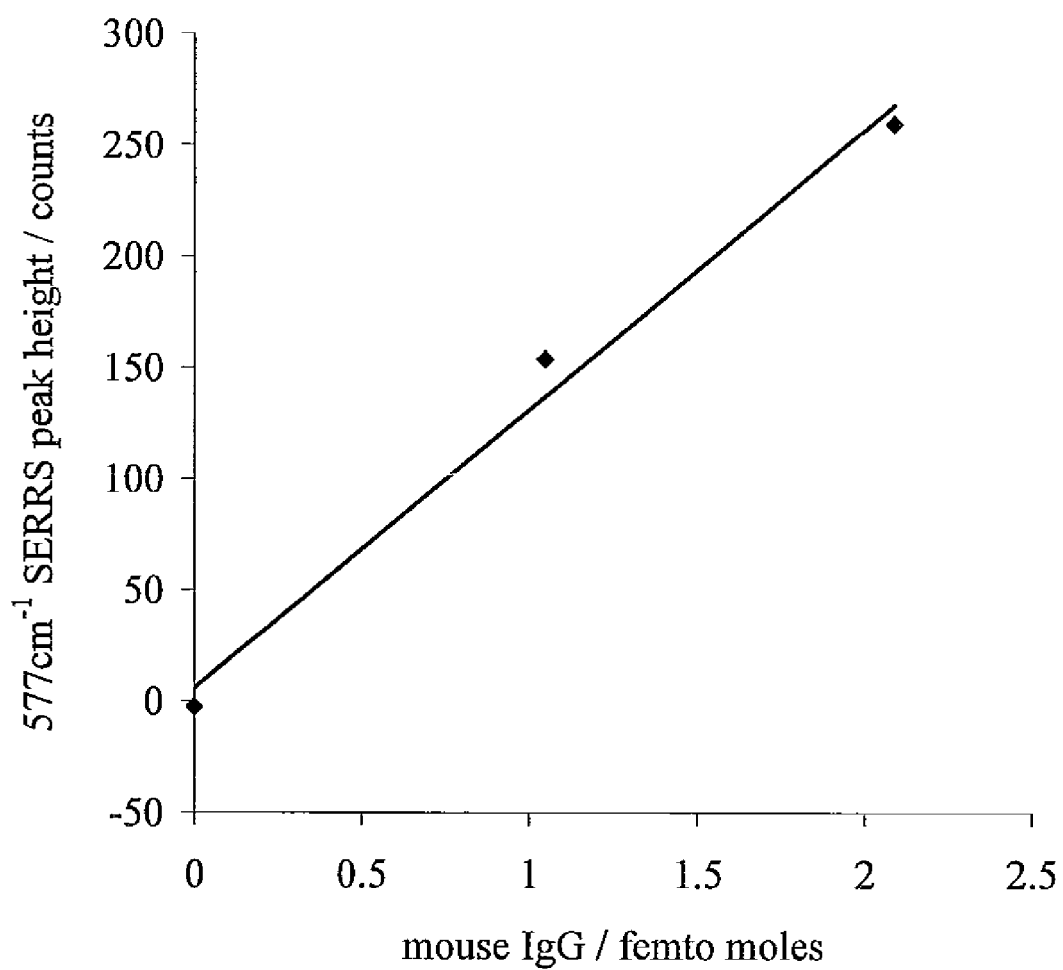
FIG. 11: Results from the immunoassay using 2e modified AuNP labels.

In order to show the utility of these dye modified nanoparticles to act as ultra sensitive labels in bioassays the nanoparticles were employed in a standard immunoassay based on mouse IgG. The capture antibody (rabbit derived anti-mouse IgG $F_c$) was coupled to a gold surface and the Raman active nanoparticle labels were modified with goat derived anti-mouse IgG $F_{ab}$. The results from the immunoassay can be seen in FIGS. 9, 10 and 11. It can be seen from FIG. 11 that the nanoparticle label based on the modified atto680 dye (2e) could still be used to detect the presence of the target antibody in the femto-molar region, however, at this level the MBA modified nanoparticle label showed no signal. The $S_c$ for the 1071 cm$^{-1}$ Raman peak for MBA is 0.18 μmol$^{-1}$ dm$^3$ s$^{-1}$ this is too low to give a signal at the target concentrations used here. This confirms that the SERRS signal enhancement provided by the linker group can lower the detection limits of the Raman based nanoparticle labels giving improved performance over standard labels.

In Examples 1-8, the dye molecule carboxy-x-rhodamine was employed. The carboxy-x-rhodamine dye was modified with the same small peptide chains composed of cysteine (Cys) followed by glycine (Gly) spacers (38). The thiol group of the Cys side chain was used to anchor the dyes to the surface of a gold nanoparticle (AuNP) and the amine terminal of the amino acid chain used to attach the dye molecule. The two dyes are compared in Table 1 below:

TABLE 1

Showing the SERRS signal intensity for two dye molecules modified with a small peptide linker. The signal intensity is shown relative to the unmodified dye and is taken from the 577 cm$^{-1}$ Raman peak for atto680 and the 1503 cm$^{-1}$ Raman peak for carboxy-x-rhodamine.

| linker group | Dye | |
| --- | --- | --- |
| | atto680 | Carboxy-x-rhodamine |
| Cys | 5 | 2 |
| Cys-Gly | 27 | 22 |
| Cys-Gly-Gly | 11 | 14 |
| No linker | 1 | 1 |

It can be seen in Table 1 that the addition of the linker group enhanced the SERRS signal from both the two dye molecules. Moreover, the ratio of the enhancement is very similar for both dyes following the average pattern of 4:25:3:1 even though the UV-Vis adsorption maximums were different for both dyes (att680 $\lambda_{max}$=680 nm, carboxy-x-rhodaime $\lambda_{max}$=568 nm). Thus, the presence of the linker enhances the SERRS signal regardless of the dye.

Thus, it is observed that varying the length of the linker length provides an ultimately optimal signal enhancement. Each system can be optimized in this manner to yield the most enhanced signal possible.

All references, including publications, patents, and patent applications, cited herein are hereby incorporated by reference to the same extent as if the disclosure each reference were individually and specifically indicated to be incorporated by reference and were set forth in its entirety herein.

REFERENCES

1. K. T. Carron, B. J. Kennedy, *Anal. Chem.*, 1995, 67, 3353-3356.
2. S. Xu, X. Ji, W. Xu, B. Zhao, X. Dou, Y. Bai, Y. Ozaki, *J. Biomed. Opt.*, 2005, 10(3), 031112, 1-12.
3. P. D. Enlow, M. Buncick, R. J. Warmack, T. Vo-Dinh, *Anal. Chem.*, 1986, 58, 1119-1123.
4. J. D. Driskell, K. M. Kwarta, R. J. Lipert, M. D. Porter, *Anal. Chem.*, 2005, 77, 19, 6147-6154.
5. S. Xu, X. Ji, W. Xu, X. Li, L. Wang, Y. Bai, B. Zhao, Y. Ozaki, *Analyst*, 2004, 129, 63-68.
6. D. S. Grubisha, R. J. Lipert, H. Y. Park, J. Driskell, M. D. Porter, *Anal. Chem.*, 2003, 75, 5936-5943.
7. K. Faulds, L. Stewart, W. E. Smith, D. Graham, *Talanta*, 2005, 67, 667-671.
8. K. Faulds, W. E. Smith, D. Graham, *Analyst*, 2005, 130, 1125-1131.
9. M. Fleischmann, P. J. Hendra, A. J. McQuillan, *Chem. Phys. Lett.*, 1974, 26, 163.
10. M. G. Albrecht, J. A. Creighton, *J. Am. Chem. Soc.*, 1977, 99, 5215.
11. D. L. Jeanmaire, R. P. Van Duyne, *J. Electroanal. Chem.*, 1977, 84, 1.
12. A. Campion, P. Kambhampati, *Chem. Soc. Rev.*, 1998, 27, 241-250.
13. M. Moskovits, *Rev. Mod. Phys.*, 1985, 57, 783-826.
14. A. Otto, I. Mrozek, H. Grabhorn, W. Akemann, *J. Phys. Condens. Matter*, 1992, 4, 1143-1212.
15. J. R. Lombardi, R. L. Birke, T. Lu, J. Xu, *J. Chem. Phys.*, 1986, 84, 4174-4180.
16. K. Nakamoto, *Coordination Chemistry Reviews*, 2002, 226, 153-165.
17. Z. Zhou, G. Wang, Z. Xu, *Appl. Phys. Lett.*, 2006, 88, 034104.
18. S. Nie, S. R. Emory, *Science*, 1997, 275, 21, 1102-1106.
19. P. Kambhampati, C. M. Child, M. C. Foster, A. Campion, *J. Chem. Phys.*, 1998, 108, 5013-5026.
20. M. J. Weaver, S. Zou, H. Y. H. Chan, *Anal. Chem.*, 2000, 72, 38A-47A.
21. T. W. Koo, S. Chan, L. Sun, X. Su, J. Zhang, A. A. Berlin, *Appl. Spectrosc.*, 2004, 58, 1401-1407.
22. Zhou et al., *Appl. Phys. Lett.*, 88, 034104, 2006
23. A. Otto, *J. Raman Spectrosc.*, 22:743, 1991
24. S. Nie, S. R. Emory, *Science*, 1997, 275, 21, 1102-1106
25. P. C. Lee, D. Meisel, *J. Phys. Chem.*, 1982, 86, 3391-3395.
26. K. C. Grabar, R. G. Freeman, M. B. Hommer, M. J. Natan, *Anal. Chem.*, 1995, 67, 735-743.
27. K. R. Brown, D. G. Walter, M. J. Natan, Chem. *Mater.*, 2000, 12, 306-313.
28. T. W. Greene, P. G. M. Wuts: Protective Groups in Organic Synthesis, 3$^{rd}$ Edition, Wily Interscience, U.S.A., 1999.
29. J. P. Badyal, A. M. Cameron, N. R. Cameron, D. M. Coe, R. Cox, B. G. Davis, L. J. Oates, G. Oye, P. G. Steel, *Tetrahedron Lett.*, 2001, 42, 8531-8533.
30. N. Hayazawa, Y. Inouye, Z. Sekkat, S. Kawata, *Chemical Physics Letters*, 2001, 335, 369-374.
31. B. C. Smith, Infrared Spectral Interpretation: A Systematic Approach, CRC Press, 1999, page 130.
32. H. Okabayashi, K. Taga, T. Yoshida, K. Ohshima, H. Etori, T. Uehara, E. Nishio, *Appl. Spectrosc.*, 1991, 45, 4, 626-631.
33. C. J. McHugh, F. T. Docherty, D. Graham, W. E. Smith, *Analyst*, 2002, 127, 838-841.
34. N. Marme, J. P. Knemeyer, Anal. Bioanal. Chem., 2007, 388, 1075-1085.
35. D. A. Watson, L. O. Brown, D. F. Gaskill, M. Naivar, S. W. Graves, S. K. Doorn., J. P. Nolan, Cytometry Part A, 2008, 73A, 119-128.
36. G. McAnally, C. McLaughlin, R. Brown, D. C. Robson, K Faulds, D. R. Tackley, W. Ewen Smith, D. Graham, Analyst, 2002, 127, 838-841.
37. B. J. Kennedy, S. Spaeth, M. Dickey, K. T. Carron, J. Phy. Chem. B, 1999, 103, 3640-3646.
38. P. Drake, H. Y. Huang, Y. J. Lin, Journal of Analytical Chemistry, Accepted 2009.

We claim:

1. A surface enhanced resonance Raman spectroscopy probe comprising
    a nanoparticle, wherein said nanoparticles is selected from the group consisting of Au nanoparticles, Au alloy particles, Ag nanoparticles and Ag alloy nanoparticles,
    a linker, wherein said linker comprises Cys, and
    a signal molecule, wherein said signal molecule is a dye,
    wherein said linker connects the signal molecule to the nanoparticle, and
    wherein said linker is chemically bonded to the nanoparticle and the signal molecule.

2. The probe according to claim 1, wherein said linker is selected from the group consisting of: Cys, Gly-Cys, and Gly-Gly-Cys.

3. The probe according to claim 1, wherein said dye is selected from the group consisting of azo dyes, anthraquinone dyes, flavonoid dyes, polyphenol dyes, fluorone dyes, rhodamine dyes, phenylpropanoid dyes, polymethine dyes, phenanthridine dyes, porphyrin dyes and triaryl dyes.

4. The probe according to claim 3, wherein said dye is rhodamine.

5. The probe according to claim 1, wherein said dye is a benzatriazole azo dye.

6. The probe according to claim 3, wherein said dye is an atto680 dye.

7. The probe according to claim 3, wherein said dye is a triaryl dye.

8. The probe according to claim 1, wherein said nanoparticle is selected from the group consisting of Au and Ag nanoparticles.

9. The probe according to claim 1, wherein said nanoparticle is produced by reaction of citrate with tetrachloroaurate.

10. The probe according to claim 1, wherein the length of the linker is variable.

11. A method of detecting a target molecule by surface enhanced resonance Raman spectroscopy, wherein said method comprises:
    providing a Raman-scattering surface having a first molecule bound thereon which specifically binds the target molecule, wherein said Raman-scattering surface comprises a metal;
    providing a sample comprising the target molecule;
    providing a probe according to claim 1, wherein said probe further comprises a second molecule which specifically binds to the target molecule;
    combining said Raman-scattering surface, said sample and said probe, whereby the first molecule specifically binds to the target molecule and the second molecule specifically binds to the target, such that the probe is connected to the Raman-scattering surface;
applying a beam of light to the Raman-scattering surface; and
measuring a signal from the scattered light.

12. The method according to claim 11, wherein said metal is selected from at least one of the group consisting of: Ag, Au and Cu.

13. The method according to claim 11, wherein one or more probes are contacted to the Raman-scattering surface, and which method further comprises:
repeating the method multiple times, wherein the length of the linker of each of the probes is different, thereby determining which length provides an optimal signal.

* * * * *